United States Patent
Havens et al.

(10) Patent No.: US 11,420,181 B2
(45) Date of Patent: Aug. 23, 2022

(54) **METHODS FOR SUPPRESSION OF AMMONIA FORMATION FROM *STAPHYLOCOCCUS-XYLOSUS* AND *STAPHYLOCOCCUS-COHNII***

(71) Applicants: Dow Global Technologies LLC, Midland, MI (US); Rohm and Haas Company, Collegeville, PA (US)

(72) Inventors: Laura Havens, Midland, MI (US); Matthew Bierman, Pearland, TX (US); Joseph A. Bonadies, Jr., Midland, MI (US); Bruce D. Hook, Lake Jackson, TX (US); Aslin Izmitli, Yardley, PA (US); Kimberly A. Surber, Lake Jackson, TX (US)

(73) Assignees: DOW GLOBAL TECHNOLOGIES LLC, Midland, MI (US); ROHM AND HAAS COMPANY, Collegeville, PA (US)

( * ) Notice: Subject to any disclaimer, the term of this patent is extended or adjusted under 35 U.S.C. 154(b) by 731 days.

(21) Appl. No.: 16/334,127

(22) PCT Filed: Sep. 28, 2017

(86) PCT No.: PCT/US2017/053867
§ 371 (c)(1),
(2) Date: Mar. 18, 2019

(87) PCT Pub. No.: WO2018/064246
PCT Pub. Date: Apr. 5, 2018

(65) Prior Publication Data
US 2019/0254251 A1    Aug. 22, 2019

Related U.S. Application Data

(60) Provisional application No. 62/401,399, filed on Sep. 29, 2016.

(51) Int. Cl.
*B01J 20/02* (2006.01)
*A61L 9/014* (2006.01)
*B01J 20/22* (2006.01)

(52) U.S. Cl.
CPC .............. *B01J 20/02* (2013.01); *A61L 9/014* (2013.01); *B01J 20/22* (2013.01); *B01J 2220/4868* (2013.01)

(58) Field of Classification Search
CPC .... B01J 20/02; B01J 20/22; B01J 2220/4868; A61L 9/014
USPC ......................................................... 502/400
See application file for complete search history.

(56) References Cited

U.S. PATENT DOCUMENTS

| | | | |
|---|---|---|---|
| 4,273,786 | A | 6/1981 | Kraskin |
| 4,405,354 | A | 9/1983 | Thomas, II et al. |
| 5,945,333 | A | 8/1999 | Rehberger |
| 2003/0220211 | A1 | 11/2003 | Stoddart et al. |
| 2005/0175577 | A1* | 8/2005 | Jenkins ................. A61L 9/014 424/76.1 |
| 2008/0173248 | A1 | 7/2008 | Pavlicek et al. |

FOREIGN PATENT DOCUMENTS

| | | |
|---|---|---|
| CN | 101972586 A | 2/2011 |
| CN | 101972586 B | 4/2012 |
| CN | 102417282 | 4/2012 |
| EP | 0048747 | 4/1982 |
| EP | 1154806 | 10/2005 |

* cited by examiner

*Primary Examiner* — Anita Nassiri-Motlagh

(57) ABSTRACT

A method for suppressing the formation of ammonia comprising providing a carrier material to a container having a headspace; providing a bacteria, an acidifier and an odor inhibitor to the carrier material, the bacteria comprising *Staphylococcus-xylosus* or *Staphylococcus-cohnii* bacteria, and the odor inhibitor comprising a salt of an aminopolycarboxylic acid compound; and applying animal waste to the carrier material; wherein there is a 5 to 98 percent improvement of ammonia content in the headspace as compared to an untreated control comprising a container containing the carrier material and the bacteria and not contain the odor inhibitor.

10 Claims, No Drawings

METHODS FOR SUPPRESSION OF AMMONIA FORMATION FROM *STAPHYLOCOCCUS-XYLOSUS* AND *STAPHYLOCOCCUS-COHNII*

BACKGROUND

Animal litter is used as a catch material for feces and urine. These biological by-products can develop strong odors due to evolution of malodorous compounds, especially ammonia. Ammonia results from microbial action on urea and/or uric acid in the animal waste.

The odor from animal litters is distressing to humans and at sufficiently high levels, may be toxic. In addition, the odor is distressing to the welfare of the animals, especially in closed environments such as poultry houses and horse stalls/barns. Moreover, emissions from animal litter may contribute to the greenhouse effect. It is desirable, therefore, to find ways of controlling odors from animal litter.

The problem addressed by this invention is a method for suppressing ammonia formation by odor-causing bacteria like *Staphylococcus-xylosus* and *Staphylococcus-cohnii*.

STATEMENT OF INVENTION

A method for suppressing the formation of ammonia comprising providing a carrier material to a container having a headspace; providing a bacteria, an acidifier and an odor inhibitor to the carrier material, the bacteria comprising *Staphylococcus-xylosus* or *Staphylococcus-cohnii* bacteria, and the odor inhibitor comprising a salt of an aminopolycarboxylic acid compound; and applying animal waste to the carrier material; wherein there is a 5 to 98 percent improvement of ammonia content in the headspace as compared to an untreated control comprising a container containing the carrier material and the bacteria and not contain the odor inhibitor.

DETAILED DESCRIPTION

Unless otherwise indicated, numeric ranges, for instance "from 2 to 10," are inclusive of the numbers defining the range (e.g., 2 and 10).

Unless otherwise indicated, ratios, percentages, parts, and the like are by weight.

The terms "prevent" or "suppress" as used herein means at least partly reducing the amount of ammonia that would otherwise be formed in animal waste in the absence of the treatment described herein and is reported as a "percent improvement". In some embodiments, the percent improvement is at least 50 percent, alternatively at least 70 percent, alternatively at least 90 percent, or alternatively 100 percent, as measured for instance by colorimetric indicators (e.g., using Drager tubes as described in the Examples), optical transmission absorption methods and/or gas chromatography in real time animal usage or laboratory testing method that mimics urine degradation. The percent improvement is relative to a system containing the same carrier material, animal waste, and bacteria as the test environment but omitting the treatment described herein (e.g., the odor inhibitor, acidifier, and any additives).

The term "animal" as used in this specification generally means non-human animals. In one instance, "animal" refers to birds. More specific examples include, without limitation, poultry (e.g., chickens, turkeys, ducks, quail, pigeons, and geese), felines, and horses.

The term "waste" refers to any animal waste product that contains compounds that may be transformed by bacteria into ammonia. In one instance, waste refers to any animal waste product that contains urea, uric acid, or both. Examples include animal urine and excrement (e.g., feces, droppings).

The present disclosure describes a method for suppressing ammonia formation. The method of the present disclosure includes providing a carrier material, an acidifier, a bacteria and an odor inhibitor to a container having a headspace. Without being limited by theory, it is anticipated that the ammonia is formed by bacteria interaction with a urea derivative, for example urea or uric acid. The bacteria used in the method of the present disclosure are bacteria of the species *Staphylococcus-xylosus* and *Staphylococcus-cohnii*. When it is stated that the bacteria are of an identified species, it is understood that bacteria naturally evolve and mutate, and as such, a bacteria is understood to be of the same species when it shares at least 97 percent of the genetic makeup with the target species.

The headspace is defined as the unfilled space above the carrier material in the container. The container is defined as any structure which is suitable for holding the carrier material. In one instance the container is the floor of a poultry house or chicken coop. In one instance, the container is a surface such as the floor of an animal stall or a room. In one instance the container is at least partially enclosed. In one instance the container is open to the surrounding area. Where the container is open to the surrounding area, headspace measurements described herein are performed in close proximity to the carrier material, for example, one to twelve inches from the upper surface of the carrier material, preferably one to six inches from the upper surface of the carrier material. The carrier material may be any material that is typically used as a bedding or absorbent for animals and their waste and includes, for instance, wood shavings, hay, straw, ground straw, wood chips, saw dust, pelletized saw dust, paper, chopped corn cobs, peanut hulls, cocoa hulls, rice hulls, wheat grass, grass, flax, oat, wheat, rye, shredded paper, walnut husks, coconut husks, sand or mixtures thereof.

In some embodiments, the animal is poultry and the carrier material is wood shavings, hay, straw, ground straw, wood chips, saw dust, pelletized saw dust, paper, chopped corn cobs, peanut hulls, cocoa hulls, rice hulls, wheat grass, grass, flax, oat, wheat, rye, shredded paper, walnut husks, coconut husks, sand or mixtures thereof.

The odor inhibitor used herein comprises a salt of an aminopolycarboxylic acid compound. As discussed above, the odor inhibitor functions by preventing formation of ammonia, an odor causing compound. Preferred cations for the salts of the invention include sodium or potassium.

In some embodiments, solutions of the aminopolycarboxylic acid salt has a pH in water from 4 to 9, preferably from 4 to 5.5, for example, VERSENE™ (available from The Dow Chemical Company) is provided as 40 weight percent solution in water.

In some embodiments, the odor inhibitor is an aminopolycarboxylic acid compound salt with an ethylenediamine or diethylenetriamine backbone.

In some embodiments, the odor inhibitor is an ethylenediaminetetraacetic salt, a diethylenetriaminepentaacetic salt, a N-hydroxyethylethylenediaminetriacetic salt, or a mixture of two or more thereof.

In some embodiments, the odor inhibitor is a sodium salt of ethylenediaminetetraacetic acid, a potassium salt of ethylenediaminetetraacetic acid, or a mixture thereof.

In some embodiments, the odor inhibitor is a sodium salt of ethylenediaminetetraacetic or a mixture of such salts. For instance, the odor inhibitor is monosodium ethylenediaminetetraacetic acid (NaEDTA), disodium ethylenediaminetetraacetic acid ($Na_2EDTA$), trisodium ethylenediaminetetraacetic acid ($Na_3EDTA$), tetrasodium ethylenediaminetetraacetic acid ($Na_4EDTA$), or a mixture of two or more thereof. In some embodiments, $Na_2EDTA$ is preferred.

In some embodiments, the odor inhibitor is a potassium salt of ethylenediaminetetraacetic acid or a mixture of such salts. For instance, the odor inhibitor is monopotassium ethylenediaminetetraacetic acid (KEDTA), dipotassium ethylenediaminetetraacetic acid ($K_2EDTA$), tripotassium ethylenediaminetetraacetic acid ($K_3EDTA$), tetrapotassium ethylenediaminetetraacetic acid ($K_4EDTA$), or a mixture of two or more thereof. In some embodiments, $K_2EDTA$ is preferred.

The acidifier is selected to cause the pH of the material that comprises the combination of the carrier material and the odor inhibitor to drop below 7. Types of acidifiers are sodium bisulfate, hydrated potassium aluminum sulfate, sulfuric acid, ferrous sulfate, citric acid and phosphoric acid.

In some embodiments, an optional liquid binder as incorporated with the carrier material. In some embodiments, the liquid binder is a liquid solution which, when combined with the odor inhibitor, the acidifier and the carrier material, forms granules such that during transport and typical use, a majority of the granules will substantially hold their shape. In some instances the liquid binder is water, salt solutions, solutions of EDTA salts, glycols, propylene glycol, glycerin, polyethylene glycol, polypropylene glycol, polyalkylene glycol lubricants, or a combination thereof. Preferably, the liquid binder is a liquid at room temperature. Preferably, the liquid binder has low toxicity.

The odor inhibitor and the acidifier are combined with the carrier material as described herein. The combination of odor inhibitor and acidifier work to suppress the ammonia gas generated and to bring the pH of the combined product into the desired range. The quantity of odor inhibitor or acidifier added is measured in weight percent (as defined as the weight percent of the odor inhibitor or the acidifier to the total weight of the combination of the carrier material, odor inhibitor, acidifier, and any other compounds added to the carrier material, such as a liquid binder or additive). In one instance, the quantity of odor inhibitor is at least 1.0 weight percent. In one instance, the quantity of odor inhibitor is at least 1.5 weight percent. In one instance, the quantity of odor inhibitor is at least 2.0 weight percent. Preferably, the quantity of odor inhibitor is at least 2.5 weight percent. In one instance, the quantity of odor inhibitor is at least 3.0 weight percent. In one instance, the quantity of odor inhibitor is at most 5.0 weight percent. In one instance, the quantity of odor inhibitor is at most 4.5 weight percent. In one instance, the quantity of odor inhibitor is at most 4.0 weight percent. In one instance, the quantity of acidifier is at least 0.5 weight percent. In one instance, the quantity of acidifier is at least 1.0 weight percent. In one instance, the quantity of acidifier is at most 4.0 weight percent. In one instance, the quantity of acidifier is at most 3.0 weight percent. In one instance, the quantity of acidifier is at most 2.0 weight percent. Preferably, the quantity of acidifier is from 0.5 to 1.5 weight percent and the quantity of odor inhibitor is from 2.0 to 3.0 weight percent. More preferably, the quantity of acidifier is from 0.7 to 1.3 weight percent and the quantity of odor inhibitor is from 2.2 to 2.8 weight percent.

In another aspect, the invention provides improved efficiency in prevention of urea degradation due to the preferred placement of the odor control agent at or near the surface of the litter particles.

The methods described herein may contain other additives, besides the odor inhibitor, the acidifier, the liquid binder, and the carrier material, that are typically used in animal litters. These additives include, but are not limited to, fillers, humectants, disintegrants, odor absorbing materials (e.g., sodium carbonate, potassium carbonate, siliceous material, opaline silica, activated carbon, sodium bisulfate complex, or corn starch), zeolite, dedusting agents (e.g., gaur gum, PTFE coated clay, or fluoropolymers), antimicrobials such as bronopol and silver based compounds, fragrances, other chelants (diethylenetriaminepentaacetic acid (DTPA) for example), gypsum, small molecule organic acids, polymers with neutralization capacity or acid groups (e.g., cellulose acetate, polyxcarboxylates), rice flour, quaternary amines, probiotic bacteria and/or ammonia oxidizing bacteria.

In some embodiments, the carrier material described herein is free of other odor preventing additives, for instance it is free of one or more of: an alkali metal tetraborate n-hydrate, alum, other transition metal salts (e.g., Zn, copper salts) and/or boron compounds. As used herein, when it is said that the carrier material is free of a compound it means that the carrier material is substantially free of that compound, for example, the carrier material contains less than 100 ppm of that compound.

The addition of the odor inhibitor and acidifier to the carrier material, as described herein, results in the prevention of ammonia formation, thereby significantly reducing undesirable animal odors. The odor inhibitor and acidifier can be incorporated with the carrier material by a variety of standard techniques known to those skilled in the art including, for instance, solids mixing (including dry blending or co-grinding), spreading, sprinkling, and the like.

For instance, in one embodiment, the odor inhibitor and acidifier may be sprinkled over the top of a bed of the carrier material. In this embodiment the bed of carrier material may be further agitated or mixed to mix the odor inhibitor and acidifier deeper into the material.

In another embodiment, the odor inhibitor and acidifier may be dry blended with the carrier material and packaged together prior to use as an animal litter. In a preferred embodiment, the odor inhibitor and acidifier are made into granules prior to dry blending such that the granules and the carrier material are of a similar size and shape so to inhibit demixing or stratification of the odor inhibitor containing particles from the carrier due to segregation.

When preparing the odor inhibitor and acidifier, it may be desirable to match the particle density as well as shape of the carrier material to reduce the likelihood of particle segregation.

Other mixing techniques may include dry briquetting the mixture of carrier material, acidifier and odor inhibitor to uniformly combine the materials (e.g., a size range from hundreds of microns to millimeters may be suitable).

In some embodiments, the odor inhibitor and acidifier may be applied to the carrier material prior to the animal releasing its waste on the carrier material. In some embodiments, the odor inhibitor and acidifier may be applied or reapplied to the carrier material for second or subsequent generations of use.

In one embodiment, the odor inhibitor and acidifier may be dry blended with the carrier material and packaged together prior to use as an animal litter. In a preferred embodiment, the odor inhibitor and acidifier are made into a fine powder prior to dry blending to enhance the coatability of the odor inhibitor onto the carrier material. The fine powder may be produced by spray drying, grinding, precipitation or combination thereof, and may be combined with a flow aid by dry blending or binding with a liquid to enhance attachment to the carrier. In another preferred embodiment, a liquid binder is mixed in with the odor inhibitor, the acidifier and the carrier to aid with binding the odor inhibitor and the acidifier onto the carrier.

In another embodiment, the carrier material may be sprayed with a binder liquid and then blended with dry odor inhibitor and acidifier so that the dry particles are attached to the carrier material by the binder liquid at a desired concentration. Likewise, the carrier material may be blended with dry odor inhibitor and acidifier and then sprayed with a binder liquid so that the dry particles are attached to the carrier material by the binder liquid at a desired concentration. The coated carrier material particles may then optionally be dried in order to evaporate water or a solvent component that may optionally be present in the binder liquid. Preferably, the liquid binder is at least partially water soluble.

In one embodiment an additive material is provided to the carrier material. In one instance, the additive material is diatomite, citrate salts, talc, gypsum, calcium carbonate, calcium bentonite, sand, glass, dirt, alumina, alumina-silicates, silicates, or a combination thereof. Preferably the additive material is combined with the carrier material, odor inhibitor and acidifier using the methods described herein.

The bacteria described herein is the naturally occurring *Staphylococcus-xylosus* or *Staphylococcus-cohnii* bacteria which is commonly present in the natural flora, as well as in animal waste. As used herein, "providing a bacteria" means that a bacteria is introduced to the system. Preferably, the bacteria is introduced to the system as part of the animal waste.

The present disclosure describes a method for suppressing the formation of ammonia comprising providing a carrier material to a container having a headspace; providing a bacteria, an acidifier and an odor inhibitor to the carrier material, the bacteria comprising *Staphylococcus-xylosus* or *Staphylococcus-cohnii* bacteria, and the odor inhibitor comprising a salt of an aminopolycarboxylic acid compound; and applying animal waste to the carrier material; wherein there is a 5 to 98 percent improvement of ammonia content in the headspace as compared to an untreated control comprising a container containing the carrier material, the animal waste and the bacteria and not containing the odor inhibitor or the acidifier. In one instance, the methods described herein results in an ammonia content of 25 ppm or less. In one instance, the methods described herein results in ammonia content of 25 ppm or less for 21 days. It is understood that the method steps, unless specifically stated otherwise, may be performed in any order and may be repeated.

The method further comprises providing an additive material to the carrier material, wherein the additive material comprises citrate salts, talc, gypsum, calcium carbonate, sand, glass, dirt, alumina, alumina-silicates, silicates, or a combination thereof. The additive material is preferably added prior to applying the animal waste.

Some embodiments of the invention will now be described in detail in the following Examples.

EXAMPLES

Examples 1, 2, 3 and 4. Lab Experiments:

Synthetic Poultry Urine Preparation. In these Examples, synthetic urine was prepared as follows for each 100 g of synthetic poultry urine needed. The amounts can be scaled up or down as needed. The following components were added to a sterilized bottle: Urea (USP Grade): 0.43 g, Ammonia: 0.46 g, $K_3PO_4$ (USP grade): 6.8 g, Milli-Q water: 83.52 g. The bottle was capped and placed on a bottle roller at ambient temperature for 1 to 3 hours. The pH of the solution was measured to confirm the pH is between 13 and 14. To add 7.5 gr of synthetic urine to the samples (Examples 1 and 2), 0.66 g USP grade uric acid and 6.84 mL of the prepared solution were added to a 50 mL centrifuge tube and vortex mixed at high setting for 15 seconds. To add 10 gr of synthetic urine to the samples (Examples 3 and 4), 0.88 g USP grade uric acid and 9.12 mL of the prepared solution were added to a 50 mL centrifuge tube and vortex mixed at high setting for 15 seconds. The pH of the mixture will be between 11 and 12 for both cases.

Bacteria Preparation. In these Examples, the *Staphylococcus-cohnii* and the *Staphylococcus-cohnii/Staphylococcus-xylosus* bacteria strains used were environmental isolates from poultry manure and cat litter respectively. As used herein, "*Staphylococcus-cohnii/Staphylococcus-xylosus*" refers to a bacteria strain that is an environmental isolate from cat feces that through DNA sequencing has been identified to be genetically similar to both *Staphylococcus-cohnii* and *Staphylococcus-xylosus*. The identifications were determined by DNA sequencing at an external lab with genus confidence level.

The bacteria strains were isolated on a sterile tryptic soy agar plate, grown for 2 days in a 30 degrees ° C. incubator and stored in a refrigerator. A fresh plate was prepared every 2 weeks.

The bacteria were grown the day before the start of the experiments by taking a loopful of the bacteria from the agar plate with a 10 uL loop and immersing it in 10 mL sterile tryptic soy broth filling half of the container. All bacteria used in the Examples are aerobic and therefore need air on top of the growth medium. The vials were incubated at 30 degrees C. in a shaking incubator at 100 rpm for 24 hours. The count of the bacteria in the growth media was determined by the serial dilutions method, where 10 serial dilutions of the growth medium in sterile Physiological Buffered Saline (PBS) solution are performed with 10× dilution each time. Each dilution was plated twice using 100 µL of growth media for each plate. The numbers of colonies were counted on the dilution plate that had between 30 and 300 colony forming units (CFU) on it. The number of colony forming units in the original growth media was then determined by back-calculating the number of dilutions. The overnight growth solution for *Staphylococcus-cohnii* and *Stapylococcus-xylosus* bacteria strains used in these experiments were ~5.2 CFU/mL and 9.9 CFU/mL respectively. All pipettes, containers, tips, spoons etc. equipment used for these experiments were sterile in order to prevent contamination with other bacteria. Litters, treatments and chemicals used for preparing synthetic urine were used as-is, without sterilization.

Preparation of grinded straw bedding. A sterilized lab blender was loaded with straw and grinded at pulsed, high setting for 15-45 seconds. Then a new batch of straw was loaded to the blender. The blender was allowed to cool when it got warm, usually after 30 minutes of grinding, to prevent the samples from heating too much.

Sample Preparation. A sterilized 1 L (ex. Tri-Pour®) container was charged with 15 g grinded straw. The litter in each test sample was leveled by tapping on the container.

For Examples 1 and 2, 7.5 g synthetic urine prepared as detailed herein was mixed with 2.28 mL MilliQ water and 1 mL of sterile phosphate buffered saline solution with a vortex mixer at high setting for 10 seconds. 1 mL of overnight bacteria growth solution prepared as detailed previously was added to the mixture and vortex mixed at high setting for 10 s.

For Examples 3 and 4, 2 mL of overnight bacteria growth solution prepared as detailed herein was added to 10 gr of synthetic urine prepared as detailed earlier and vortex mixed at high setting for 10 s.

The synthetic urine and bacteria mixture was immediately added to the sample after preparation and mixed with the straw using a sterile inoculation loop. The sample were then covered with aluminum foil to prevent vapors from escaping the container. The ammonia levels in the headspace were measured on days 1 and 4 after inoculation.

Adding the Treatments:

After the measurements on day 4, the aluminum foil on the samples were opened and the desired treatments were added. The aluminum foil was opened for the same amount of time for the untreated control samples.

Treatments for the several Examples are detailed below; Table 1 details which treatment applies to each specific Example.

Treatments for Examples 1 and 2:

1% sodium bisulfate: Add 1% by weight sodium bisulfate on the bedding and mix with a sterile loop.

1% sodium bisulfate+2.5% Na$_2$EDTA solid: Add 1% by weight sodium bisulfate and 2.5% by weight Na$_2$EDTA on the bedding and mix with a sterile loop.

Treatments for Examples 3 and 4:

1% sodium bisulfate: 1% by weight solid sodium bisulfate was applied on the bedding and mixed with a sterile loop.

2.5% K$_2$EDTA: 40% active K$_2$EDTA solution was added to the bedding to get 2.5% active and mixed with a sterile loop.

1% sodium bisulfate+2.5% K2EDTA: 1% by weight solid SODIUM BISULFATE and 40% active K$_2$EDTA was added to the bedding to get 2.5% active were added to the bedding and mixed with a sterile loop 1% sodium bisulfate sprinkled on top: 1% by weight solid sodium bisulfate was sprinkled on the bedding (not mixed).

2.5% K$_2$EDTA sprayed on top: 40% active K$_2$EDTA solution was sprayed on the bedding to get 2.5% active (not mixed).

After treatment, the samples were again sealed with aluminum foil. Headspace ammonia levels were measured as described herein again on days 5, 7 and 11 and 21 after inoculation (These correspond to days 1, 3 and 7 and 17 after treatment).

Headspace Ammonia Measurement. The ammonia in the headspace of each test container was sampled using a SENSIDYNE® AP-20S Aspirating Detector Tube Pump. Low (0.2-20 ppm), medium 1 (5-260 ppm), medium 2 (1-200 ppm) or high (50-900 ppm) range SENSIDYNE® Ammonia Gas Detector Tubes were used to quantify the headspace ammonia concentration. The following procedure was used for ammonia detection and quantification in each test sample. 1. Break both ends of the detector tube using the breaking port on pump. 2. Point the arrow mark on the detector tube towards the aspirating pump. Insert the detector tube securely into the rubber tube connector of the aspirating pump. 3. To sample the test headspace, pierce a small hole in the center of the aluminum foil cover of the test sample. Insert the detector tube (attached to the aspirating pump) into the sampling hole to the specified measurement distance. Insert the tube into the headspace to 45 mm, (equal to the thick blue line on the bottom end of the gas detector tube). 4. Hold the pump at the 45 mm measurement distance. Pull the pump handle at full stroke to the locked position. Wait for 1 minute until sampling is complete which is confirmed with the flow indicator of the pump. The instruction manual of the aspirating pump will give more details if necessary. 5. Read the scale at the maximum point of the stained layer (yellow in color). Read and report the concentration immediately after measurement. If the reading is off scale, for example 20 ppm for the low range tubes, repeat the measurement using the medium range gas detector tube. If the reading is off scale for the medium range tubes, use the high range tubes. 6. After sampling, seal the sampling hole in the aluminum foil cover with tape.

The headspace ammonia levels after treatment for the Examples 1 and 2 are reported in Table 1 and the headspace ammonia levels after treatment for the Examples 3 and 4 are reported in Table 2. For Examples 3 and 4, the medium 1 and high level ammonia tubes were not available and headspace ammonia levels were measured with tubes that had a maximum measurement threshold of 200 ppm. The results reported as 200+ were higher levels of ammonia in the headspace that could not be measured.

All samples were prepared in triplicates. Average values of 3 replicates were reported. The ammonia content in the headspace was reported as a percent improvement. The percent improvement was calculated as the percent decrease of ammonia in the headspace as compared to a control containing the same bacteria strain and concentration tested using the procedure above except omitting the odor inhibitor and acidifier. If both control and treated sample had headspace ammonia levels that was larger than 200 ppm (200+), the percent improvement in headspace ammonia was reported as "?", since no comparison could be made in these cases.

TABLE 1

| Example number | Bacteria | Treatment | Days after treatment | % improvement in headspace ammonia | Headspace ammonia in untreated control sample (ppm) |
|---|---|---|---|---|---|
| 1 | Staphylococcus-cohnii | 1% sodium bisulfate | 1 | 78 | 85 |
| 1 | Staphylococcus-cohnii | 1% sodium bisulfate + 2.5% Na$_2$EDTA | 1 | 89 | 85 |
| 1 | Staphylococcus-cohnii | 1% sodium bisulfate | 3 | 9 | 177 |
| 1 | Staphylococcus-cohnii | 1% sodium bisulfate + 2.5% Na$_2$EDTA | 3 | 78 | 177 |
| 1 | Staphylococcus-cohnii | 1% sodium bisulfate | 7 | −1 | 250 |

TABLE 1-continued

| Example number | Bacteria | Treatment | Days after treatment | % improvement in headspace ammonia | Headspace ammonia in untreated control sample (ppm) |
|---|---|---|---|---|---|
| 1 | Staphylococcus-cohnii | 1% sodium bisulfate + 2.5% Na$_2$EDTA | 7 | 41 | 250 |
| 2 | Staphylococcus-cohnii | 1% sodium bisulfate | 1 | 85 | 70 |
| 2 | Staphylococcus-cohnii | 1% sodium bisulfate + 2.5% Na$_2$EDTA | 1 | 88 | 70 |
| 2 | Staphylococcus-cohnii | 1% sodium bisulfate | 3 | 7 | 140 |
| 2 | Staphylococcus-cohnii | 1% sodium bisulfate + 2.5% Na$_2$EDTA | 3 | 64 | 140 |
| 2 | Staphylococcus-cohnii | 1% sodium bisulfate | 7 | −10 | 217 |
| 2 | Staphylococcus-cohnii | 1% sodium bisulfate + 2.5% Na$_2$EDTA | 7 | 23 | 217 |
| 2 | Staphylococcus-cohnii | 1% sodium bisulfate | 17 | 38 | 403 |
| 2 | Staphylococcus-cohnii | 1% sodium bisulfate + 2.5% Na$_2$EDTA | 17 | 40 | 403 |

TABLE 2

| Example number | Bacteria | Treatment | Days after treatment | % improvement in headspace ammonia | Headspace ammonia in untreated control sample |
|---|---|---|---|---|---|
| 3 | Staphylococcus-cohnii | 1% sodium bisulfate | 1 | 53 | 123 |
| 3 | Staphylococcus-cohnii | 2.5% K$_2$EDTA | 1 | 64 | 123 |
| 3 | Staphylococcus-cohnii | 1% sodium bisulfate + 2.5% K$_2$EDTA | 1 | 72 | 123 |
| 3 | Staphylococcus-cohnii | 1% sodium bisulfate sprinkled on top | 1 | 87 | 123 |
| 3 | Staphylococcus-cohnii | 2.5% K$_2$EDTA sprayed on top | 1 | 64 | 123 |
| 3 | Staphylococcus-cohnii | 1% sodium bisulfate | 3 | ? | 200+ |
| 3 | Staphylococcus-cohnii | 2.5% K$_2$EDTA | 3 | 8+ | 200+ |
| 3 | Staphylococcus-cohnii | 1% sodium bisulfate + 2.5% K$_2$EDTA | 3 | 26+ | 200+ |
| 3 | Staphylococcus-cohnii | 1% sodium bisulfate sprinkled on top | 3 | ? | 200+ |
| 3 | Staphylococcus-cohnii | 2.5% K$_2$EDTA sprayed on top | 3 | 5+ | 200+ |
| 4 | Staphylococcus-xylosus/Staphylococcus-cohnii | 1% sodium bisulfate | 1 | 41 | 131 |
| 4 | Staphylococcus-xylosus/Staphylococcus-cohnii | 2.5% K$_2$EDTA | 1 | 73 | 131 |
| 4 | Staphylococcus-xylosus/Staphylococcus-cohnii | 1% sodium bisulfate + 2.5% K$_2$EDTA | 1 | 91 | 131 |
| 4 | Staphylococcus-xylosus/Staphylococcus-cohnii | 1% sodium bisulfate sprinkled on top | 1 | 87 | 131 |
| 4 | Staphylococcus-xylosus/Staphylococcus-cohnii | 2.5% K$_2$EDTA sprayed on top | 1 | 57 | 131 |
| 4 | Staphylococcus-xylosus/Staphylococcus-cohnii | 1% sodium bisulfate | 3 | ? | 200+ |

TABLE 2-continued

| Example number | Bacteria | Treatment | Days after treatment | % improvement in headspace ammonia | Headspace ammonia in untreated control sample |
|---|---|---|---|---|---|
| 4 | Staphylococcus-xylosus/ Staphylococcus-cohnii | 2.5% K$_2$EDTA | 3 | 12+ | 200+ |
| 4 | Staphylococcus-xylosus/ Staphylococcus-cohnii | 1% sodium bisulfate + 2.5% K$_2$EDTA | 3 | 49+ | 200+ |
| 4 | Staphylococcus-xylosus/ Staphylococcus-cohnii | 1% sodium bisulfate sprinkled on top | 3 | 10+ | 200+ |
| 4 | Staphylococcus-xylosus/ Staphylococcus-cohnii | 2.5% K$_2$EDTA sprayed on top | 3 | ? | 200+ |

These Examples illustrate generally that the combination of an odor inhibitor (such as K$_2$EDTA) and an acidifier (such as sodium bisulfate) provides improved ammonia neutralization as compared to the use of only an odor inhibitor or an acidifier.

Examples 5-8. Barrel Test Experiments:

Used litter (rice hulls which may also contain poultry manure, moisture, feed residue and/or feathers) were acquired from a commercial broiler chicken farm and transported in plastic barrels. Twenty three kilograms of litter were weighed into 0.4 m² plastic tubs to cover the tubs to a depth of approximately 10 cm. The tubs were stored uncovered in a poultry rearing facility, and environmental conditions were controlled to mimic the conditions that would be experienced in a commercial broiler house (temperature around 32° C.).

Example 5. Comparative Example:

Tubs were treated with NaHSO$_4$ at a dose equivalent to 1 wt % Ammonia was then measured for 35 days.

Example 6:

Tubs were treated in two steps. A dose equivalent to 1 wt % of NaHSO$_4$ as Acidifier was added to the tubs. After 24 hours, a dose equivalent to 3.2 wt % of Na$_2$EDTA was added and dispersed. Ammonia was then measured for 35 days.

Example 7:

Tubs were treated in two steps. A dose equivalent to 1 wt % of NaHSO$_4$ as Acidifier was added to the tubs. After 24 hours, a dose equivalent to 3.2 wt % of K$_2$EDTA was added as an aqueous solution. Ammonia was then measured for 35 days.

Example 8:

Tubs were treated in two steps. A dose equivalent to 1.23 wt % of EDTA Acid was added to the tubs. After 24 hours, a dose equivalent to 3.2 wt % of Na$_2$EDTA was added and dispersed. Ammonia was then measured for 35 days.

The results for Examples 5 through 8 are reported in Table 3.

TABLE 3

| Example number | Treatment | Days after treatment | % improvement in headspace ammonia | Ave headspace ammonia in untreated control sample (ppm) |
|---|---|---|---|---|
| 5 | 1 wt % NaHSO$_4$ | 3 | 92% | 87 |
| 5 | 1 wt % NaHSO$_4$ | 7 | 74% | 87 |
| 5 | 1 wt % NaHSO$_4$ | 14 | 37% | 87 |
| 5 | 1 wt % NaHSO$_4$ | 21 | −37% | 87 |
| 5 | 1 wt % NaHSO$_4$ | 28 | −16% | 87 |
| 6 | 1 wt % NaHSO$_4$ 3.2 wt % Na$_2$EDTA | 3 | 96% | 87 |
| 6 | 1 wt % NaHSO$_4$ 3.2 wt % Na$_2$EDTA | 7 | 89% | 87 |
| 6 | 1 wt % NaHSO$_4$ 3.2 wt % Na$_2$EDTA | 14 | 60% | 87 |
| 6 | 1 wt % NaHSO$_4$ 3.2 wt % Na$_2$EDTA | 21 | 78% | 87 |
| 6 | 1 wt % NaHSO$_4$ 3.2 wt % Na$_2$EDTA | 28 | 54% | 87 |
| 7 | 1 wt % NaHSO$_4$ 3.2 wt % K$_2$EDTA | 3 | 95% | 87 |
| 7 | 1 wt % NaHSO$_4$ 3.2 wt % K$_2$EDTA | 7 | 94% | 87 |
| 7 | 1 wt % NaHSO$_4$ 3.2 wt % K$_2$EDTA | 14 | 78% | 87 |
| 7 | 1 wt % NaHSO$_4$ 3.2 wt % K$_2$EDTA | 21 | 82% | 87 |

TABLE 3-continued

| Example number | Treatment | Days after treatment | % improvement in headspace ammonia | Ave headspace ammonia in untreated control sample (ppm) |
|---|---|---|---|---|
| 7 | 1 wt % NaHSO$_4$ 3.2 wt % K$_2$EDTA | 28 | 35% | 87 |
| 8 | 1.23 wt % EDTA Acid 3.2 wt % Na$_2$EDTA | 3 | 95% | 87 |
| 8 | 1.23 wt % EDTA Acid 3.2 wt % Na$_2$EDTA | 7 | 93% | 87 |
| 8 | 1.23 wt % EDTA Acid 3.2 wt % Na$_2$EDTA | 14 | 79% | 87 |
| 8 | 1.23 wt % EDTA Acid 3.2 wt % Na$_2$EDTA | 21 | 88% | 87 |
| 7 | 1.23 wt % EDTA Acid 3.2 wt % Na$_2$EDTA | 28 | 77% | 87 |

These Examples illustrate generally that the combination of an odor inhibitor (such as K$_2$EDTA) and an acidifier (such as NaHSO$_4$) provides improved ammonia neutralization as compared to the use of only an acidifier.

What is claimed is:

1. A method for suppressing the formation of ammonia comprising:
providing a carrier material to a container having a headspace;
providing an acidifier and an odor inhibitor to the carrier material, the odor inhibitor comprising a sodium or potassium salt of an aminopolycarboxylic acid compound; and
applying animal waste to the carrier material; wherein the animal waste comprises *Staphylococcus-xylosus* or *Staphylococcus-cohnii* bacteria, and wherein there is a 5 to 98 percent improvement of ammonia content in the headspace as compared to an untreated control comprising a container containing the carrier material and the bacteria and not contain the odor inhibitor.

2. The method of claim 1, the method further comprising: providing an additive material to the carrier material, wherein the additive material comprises diatomite, citrate salts, talc, gypsum, calcium carbonate, sand, glass, dirt, alumina, alumina-silicates, silicates, or a combination thereof.

3. The method of claim 1, wherein the odor inhibitor is a salt of an aminopolycarboxylic acid compound having an ethylenediamine or diethylenetriamine backbone.

4. The method claim 1, wherein the odor inhibitor is a salt of ethylenediaminetetraacetic acid, a salt of diethylenetriaminepentaacetic acid, a salt of N-hydroxyethylethylenediaminetriacetic acid, or a mixture of two or more thereof.

5. The method of claim 1, wherein the carrier material is non-porous.

6. The method of claim 1, wherein the animal waste contains urea or uric acid.

7. The method of claim 1, wherein the odor inhibitor comprises 1.0 to 5.0 weight percent of the combination of the acidifier, the odor inhibitor and the carrier material.

8. The method of claim 1, wherein the acidifier comprises 0.5 to 4.0 weight percent of the combination of the acidifier, the odor inhibitor and the carrier material.

9. The method of claim 1 wherein the carrier is wood shavings, hay, straw, ground straw, wood chips, saw dust, pelletized saw dust, paper, chopped corn cobs, peanut hulls, cocoa hulls, rice hulls, wheat grass, grass, flax, oat, wheat, rye, shredded paper, walnut husks, coconut husks, sand or mixtures thereof.

10. The method of claim 1, wherein the acidifier is sodium bisulfate, hydrated potassium aluminum sulfate, sulfuric acid, ferrous sulfate, or phosphoric acid.

* * * * *